United States Patent
Yada et al.

(10) Patent No.: US 7,166,741 B2
(45) Date of Patent: Jan. 23, 2007

(54) PROCESS FOR PRODUCING (METH) ACRYLIC ACID COMPOUND

(75) Inventors: Shuhei Yada, Mie (JP); Yasushi Ogawa, Mie (JP); Kenji Takasaki, Mie (JP); Yoshiro Suzuki, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/837,177

(22) Filed: May 3, 2004

(65) Prior Publication Data
US 2005/0059838 A1    Mar. 17, 2005

Related U.S. Application Data

(63) Continuation of application No. PCT/JP03/11205, filed on Sep. 2, 2003.

(30) Foreign Application Priority Data
Sep. 3, 2002    (JP)    .............................. 2002-257275

(51) Int. Cl.
*C07C 69/52* (2006.01)
*C07C 67/48* (2006.01)
*C07C 51/42* (2006.01)

(52) U.S. Cl. ...................................... 560/218; 562/600
(58) Field of Classification Search ................ 560/218; 562/600
See application file for complete search history.

(56) References Cited

U.S. PATENT DOCUMENTS

| 5,728,272 A | 3/1998 | Hammon et al. |
| 6,179,966 B1 | 1/2001 | Shimizu et al. |

(Continued)

FOREIGN PATENT DOCUMENTS

CN    1269348 A    10/2000

(Continued)

OTHER PUBLICATIONS

U.S. Appl. No. 11/226,360, filed Sep. 15, 2005, Yada et al.
U.S. Appl. No. 11/434,067, filed May 16, 2006, Yada et al.

*Primary Examiner*—Thurman K. Page
*Assistant Examiner*—Chukwuma Nwaonicha
(74) *Attorney, Agent, or Firm*—Oblon, Spivak, McClelland, Maier & Neustadt, P.C.

(57) ABSTRACT

A process for producing a (meth)acrylic acid compound, which comprises distilling acrylic acid, methacrylic acid (these will hereinafter generally be referred to as "(meth) acrylic acid") or an ester thereof (these will hereinafter generally be referred to as "a (meth)acrylic acid compound") in a distillation column to obtain a purified (meth)acrylic acid compound, characterized in that in the course of operation of the distillation column including suspension and resumption of the operation, the distillation column is washed with water and, thereafter, inside washing with an organic solvent and/or azeotropic distillation in the presence of the organic solvent is conducted. In some cases, washing with alkaline water may be added prior to the washing with water. Washing of the distillation column for separating and purifying a crude (meth)acrylic acid compound, can be carried out easily. In particular, in a process for producing a (meth)acrylic acid compound, a substance used in a step before or after the distillation column can be utilized to recover a valuable substance, and the distillation column can be efficiently cleaned.

13 Claims, 5 Drawing Sheets

U.S. PATENT DOCUMENTS

| | | |
|---|---|---|
| 6,396,140 B1 * | 5/2002 | Juneja et al. ............... 257/700 |
| 6,413,379 B1 * | 7/2002 | Machhammer et al. ....... 203/49 |
| 6,448,438 B1 | 9/2002 | Yada et al. |
| 6,695,928 B1 | 2/2004 | Nakahara et al. |
| 2005/0059838 A1 | 3/2005 | Yada et al. |

FOREIGN PATENT DOCUMENTS

| | | |
|---|---|---|
| DE | 102 13 027 A1 | 3/2003 |
| EP | 1 033 359 A2 | 9/2000 |
| JP | 8-134012 A | 5/1996 |
| JP | 9-110779 | 4/1997 |
| JP | 2000-319223 | 11/2000 |
| JP | 2001-520214 | 10/2001 |
| JP | 2003-183220 | 9/2003 |
| WO | WO 99/20595 | 4/1999 |
| WO | WO 03/031384 A1 | 4/2003 |

* cited by examiner

PROCESS FOR PRODUCING (METH) ACRYLIC ACID COMPOUND

TECHNICAL FIELD

The present invention relates to a process for purification by distillation of acrylic acid, methacrylic acid or their esters. Particularly, the present invention relates to a washing method at the time of suspension or resumption of operation of a distillation column, which is required at the time of separating and purifying by distillation crude acrylic acid, methacrylic acid or their esters, obtainable by a vapor phase catalytic oxidation of propylene, propane or isobutylene. Hereinafter, in the present invention, acrylic acid and methacrylic acid may generally be referred to as "(meth) acrylic acid". Further, (meth)acrylic acid and its ester may generally be referred to as "a (meth)acrylic acid compound".

BACKGROUND ART

A distillation method is common as a method for separating and purifying an acryl monomer such as a (meth) acrylic acid compound. In recent years, a high performance packing material has been developed for the purpose of e.g. improving the separation efficiency by distillation or increasing the amount to be treated and has been practically employed in distillation columns in various processes. However, a (meth)acrylic acid compound is extremely polymerizable, and formation of a polymer in a distillation column has been a serious problem in a conventional tray type distillation column, particularly in a high performance packed column.

Heretofore, it is known to improve the tray structure (e.g. JP-A-2000-300903) as a method for preventing formation of a polymer of a (meth)acrylic acid compound. Further, a method of using a special polymerization inhibitor (e.g. JP-A-7-53449) has been proposed. However, it has been difficult to conduct a continuous operation for a long period of time, and periodical inspection, washing, repair, etc. have been required, which require suspension of the operation.

As a method for such washing or repair, a method has been proposed which comprises washing with a basic solution of e.g. sodium hydroxide or potassium hydroxide, followed by washing with a solvent (particularly preferably water) (e.g. JP-A-2000-319223). In a case where a (meth) acrylic acid compound is thus treated by a distillation column, it is common to finally wash the interior with water for the purpose of safety, in order to inspect the distillation column during the suspension.

At the time of resuming the operation after completion of the inspection, etc. of the distillation column washed with water as mentioned above, if such water remains in the system, the time after the resumption of the operation until the distillation column becomes stabilized in a steady condition, will be prolonged, and a non-steady operational composition state has to be continued. It has been found that continuation of this non-steady state brings about polymerization of the (meth)acrylic acid compound which is a polymerizable substance.

Thus, the object of the present invention is to provide a process for washing a distillation column for separating and purifying a crude (meth)acrylic acid compound. Particularly, in a process for producing a (meth)acrylic acid compound, it is to provide a method for cleaning the distillation column efficiently in a short time and recovering a valuable substance, by utilizing a substance used in a process before and after the distillation column.

DISCLOSURE OF THE INVENTION

As a result of an extensive study to solve the above problems, the present inventors have found various facts such as the following, and have accomplished the present invention;

(1) The obstruent in the distillation column is composed mainly of an acidic polymer formed by polymerization of a (meth)acrylic acid compound, and it will be easily swelled or dissolved with alkaline water.

(2) For removal of an alkali component, washing with water is effective.

(3) If water is present in a substantial amount in the distillation column, after resumption of the operation, it takes a long time until the operation will be in a steady operational condition.

(4) In an unstable period after resumption of the operation, formation of the polymer is substantial.

(5) Formation of the polymer can remarkably be suppressed by removing water in the distillation column.

(6) A substance used in a process before or after the distillation column, can efficiently be utilized as a dehydrating agent.

(7) If an alkali component remains, the (meth)acrylic acid compound may decomposed.

Namely, the gist of the present invention resides in a process for producing a (meth)acrylic acid compound, which comprises distilling a (meth)acrylic acid compound in a distillation column to obtain a purified (meth)acrylic acid compound, characterized in that in the course of operation of the distillation column including suspension and resumption of the operation, the distillation column is washed with water and, thereafter, inside washing with an organic solvent and/or azeotropic distillation in the presence of the organic solvent is conducted.

Further, another gist of the present invention resides in a process for producing (meth)acrylic acid, which comprises subjecting propylene, propane or isobutylene to vapor phase catalytic oxidation to obtain an oxidized reaction mixture, absorbing the oxidized reaction product in water to obtain an aqueous solution containing (meth)acrylic acid, concentrating the aqueous solution in the presence of an azeotropic agent, and distilling the obtained (meth)acrylic acid in a distillation column to obtain purified (meth)acrylic acid, characterized in that in the course of operation of the distillation column including suspension and resumption of the operation, the distillation column is washed with water and, thereafter, azeotropic distillation is conducted in the presence of the azeotropic agent.

Further, another gist of the present invention resides in a process for producing (meth)acrylic acid, which comprises subjecting propylene, propane or isobutylene to vapor phase catalytic oxidation to obtain an oxidized reaction mixture, absorbing the oxidized reaction product in water to obtain an aqueous solution containing (meth)acrylic acid, concentrating the aqueous solution in the presence of an azeotropic agent, and distilling the obtained (meth)acrylic acid in a distillation column to obtain purified (meth)acrylic acid, characterized in that in the course of operation of the distillation column including suspension and resumption of the operation, the distillation column is preliminarily washed with water, then, with alkaline water and with water and, thereafter, azeotropic distillation is conducted in the presence of the azeotropic agent.

DESCRIPTION OF REFERENCE SYMBOLS

Figure 1:
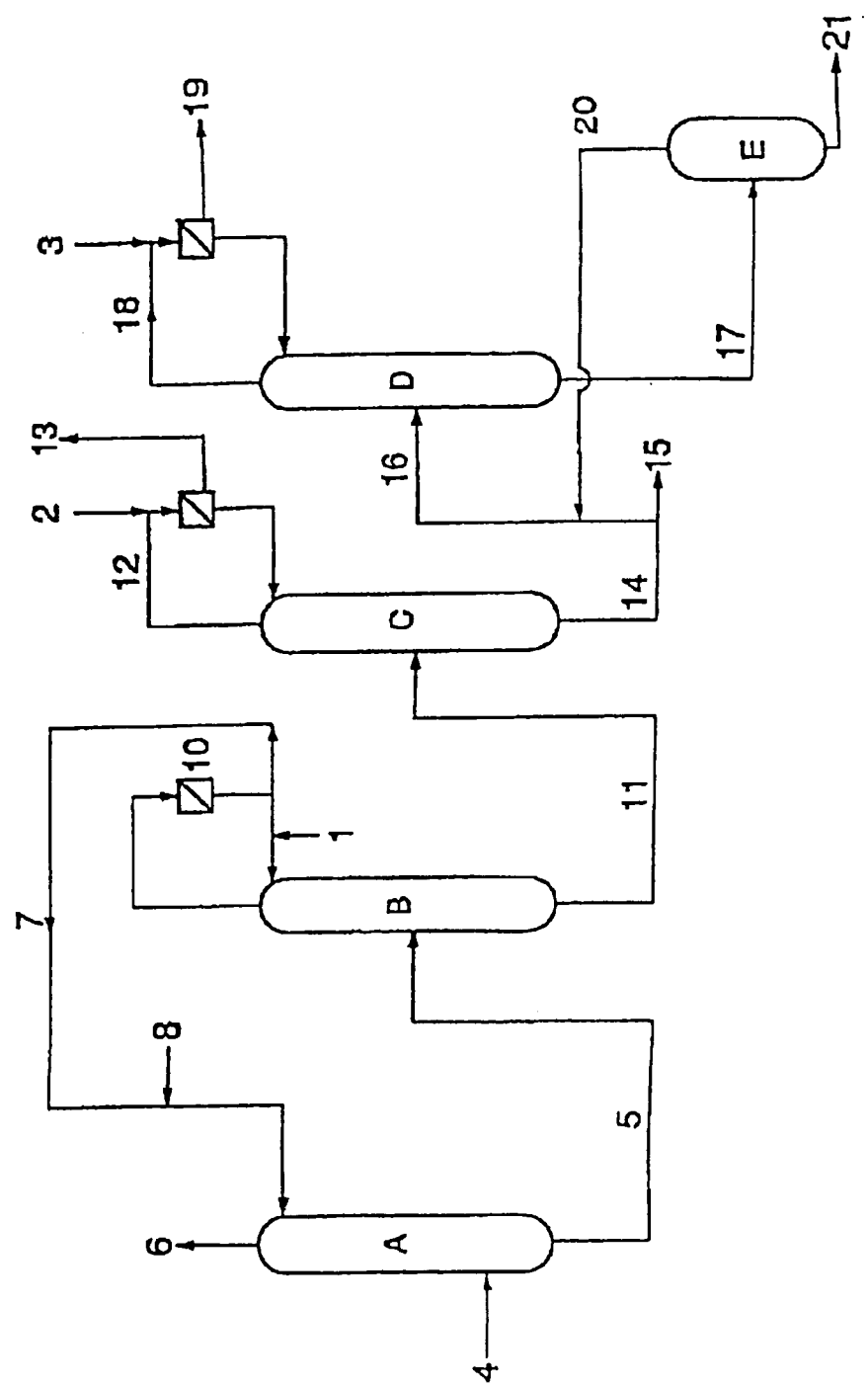
FIG. 1 is an example of a process flow chart for producing acrylic acid by using propylene as the starting material.

A: Acrylic acid collection column
B: Dehydration column
C: Low boiling separation column (acetic acid separation column)
D: High boiling separation column (acrylic acid purification column)
E: High boiling decomposition reactor
F: Distillation column having the dehydration column B and the low boiling separation column (acetic acid separation column) C joined into one column
G: Desorption column
H: High boiling removal column
K: Solvent recovery column
L: Esterification reactor
M: Acrylic acid separation column
N: High boiling decomposition reactor
Q: Alcohol extraction column
P: Alcohol recovery column
R: Low boiling separation column
S: Ester purification column

BEST MODE FOR CARRYING OUT THE INVENTION

The mixture to be treated by distillation in the present invention is acrylic acid, methacrylic acid or their esters, i.e. (meth)acrylic acid compounds. For example, acrylic acid may be mentioned which is obtained by vapor phase catalytic oxidation of propylene in the presence of a Mo—Bi type composite oxide catalyst to form acrolein, followed by vapor phase catalytic oxidation in the presence of a Mo—V type composite oxide catalyst. In such a case, the process may be a two step reaction wherein a preliminary reaction of oxidizing propylene to form mainly acrolein and a subsequent reaction of oxidizing acrolein to form mainly acrylic acid, are carried out in separate reactors, respectively, or one step reaction wherein a catalyst for the preliminary reaction and the catalyst for the subsequent reaction are simultaneously packed into one reactor to carry out the reactions. Further, the present invention is also applicable to a process for producing acrylic acid, which is obtainable by vapor phase oxidation of propane by means of a Mo—V—Te type composite oxide catalyst or a Mo—V—Sb type composite oxide catalyst. Further, an acrylic acid ester or a methacrylic acid ester may be mentioned which is obtainable in a step of producing such an ester by using (meth)acrylic acid as the starting material.

The acrylic acid ester may, for example, be methyl acrylate, ethyl acrylate, butyl acrylate, isobutyl acrylate, tert-butyl acrylate, 2-ethylhexyl acrylate, 2-hydroxyethyl acrylate, 2-hydroxypropyl acrylate, or methoxyethyl acrylate. Also with respect to the methacrylic acid ester, similar compounds may be mentioned.

The reaction mixture of the above-mentioned vapor phase catalytic oxidation is absorbed in water to obtain an aqueous solution containing (meth)acrylic acid. Such an aqueous solution is concentrated in the presence of an azeotropic agent such as an alcohol, a ketone or an aromatic hydrocarbon, whereby crude (meth)acrylic acid can be obtained. As the azeotropic agent, methyl ethyl ketone, methyl isobutyl ketone, benzene, toluene or isopropyl acetate is particularly preferred.

Such non-purified (meth)acrylic acid compounds include high boiling point impurities such as a dimer and trimer of (meth)acrylic acid, their esterified products, maleic anhydride, benzaldehyde, β-hydroxypropionic acid, β-hydroxypropionic acid esters, β-alkoxypropionic acid and β-alkoxypropionic acid esters. The content of the (meth)acrylic acid compound to be supplied to the distillation column is usually at least 2 wt %, preferably at least 5 wt %, more preferably at least 10 wt %, in the present invention. In spite of the low concentration of the (meth)acrylic acid compound, such impurities and (or) a mixed composition formed together with water, are often extremely polymerizable under the temperature and pressure conditions in the column for the distillation treatment. Yet, such a polymerization phenomenon is likely to occur at the initial stage of the distillation operation. Accordingly, the applicable range of the present invention is wide, and the present invention provides a substantial effect even in treatment of a process solution containing a small amount of (meth)acrylic acid compound.

Namely, distillation of a (meth)acrylic acid compound in the present invention is usually a step (purification step) of obtaining a high purity (meth)acrylic acid compound, but is not limited thereto, and it is applicable also to a step (separation step) of recovering a component rich in a (meth)acrylic acid compound from a mixture containing the (meth)acrylic acid compound.

Now, the present invention will be described with reference to the drawings.

FIG. 1 is an example of a process flow chart for producing acrylic acid by using propylene as the starting material. The symbols and numbers in the Fig. are as follows.

A: Acrylic acid collection column
B: Dehydration column
C: Low boiling separation column (acetic acid separation column)
D: High boiling separation column (acrylic acid purification column)
E: High boiling decomposition reactor
1 to 3: Washing solution or polymerization inhibitor-supply line
4: Oxidation reaction gas containing acrylic acid
5: Aqueous acrylic acid solution
11: Crude acrylic acid
15: Acrylic acid discharge line
19: High purity acrylic acid discharge line An acrylic acid-containing gas obtained by vapor phase catalytic oxidation of propylene and/or acrolein by using a molecular oxygen-containing gas, is introduced via a line 4 into an acrylic acid collection column A and contacted with water to obtain an aqueous acrylic acid solution.

Then, the aqueous acrylic acid solution is supplied to a dehydration column B. In the dehydration column, an azeotropic agent is supplied, an azeotropic mixture comprising water and the azeotropic agent is distilled from the column top, and acrylic acid containing acetic acid, is obtained from the column bottom. The azeotropic mixture comprising water and the azeotropic agent, distilled from the top of the dehydration column is introduced into a storage tank 10, wherein it is separated into an organic phase composed mainly of the azeotropic agent and an aqueous phase composed mainly of water. The organic phase is recycled to the dehydration column B. On the other hand, the aqueous phase is recycled via a line 7 to the acrylic acid collection column A and used as collection water to be contacted with the acrylic acid-containing gas, whereby it can be effectively utilized. Water is resupplied from a line 8, as the case requires.

The crude acrylic acid withdrawn from the bottom of the dehydration column B via a line 11, is introduced into a low boiling separation column (acetic acid separation column) C in order to remove the remaining acetic acid. Here, acetic acid is separated and removed from the column top via lines 12 and 13. Acetic acid in the line 13 contains acrylic acid, and therefore, a part or the entire amount may sometimes be returned to the process. On the other hand, acrylic acid containing substantially no acetic acid, is obtained from the column bottom via a line 14. This acrylic acid has a considerably high purity and may be used as it is, as a material for production of an acrylic acid ester, and in some cases, will be obtained as a product via a line 15. Acrylic acid of a still higher purity can be obtained by introducing it via a line 16 into a high boiling separation column (acrylic acid purification column) D to separate and remove high boiling point substances from a line 17 and to obtain highly pure acrylic acid via lines 18 and 19. The high boiling substances of the line 17 are led to a high boiling point decomposition reactor E, whereby a part is recovered as acrylic acid to the process via a line 20. The high boiling substances will be separated and removed by a line 21.

Figure 2:
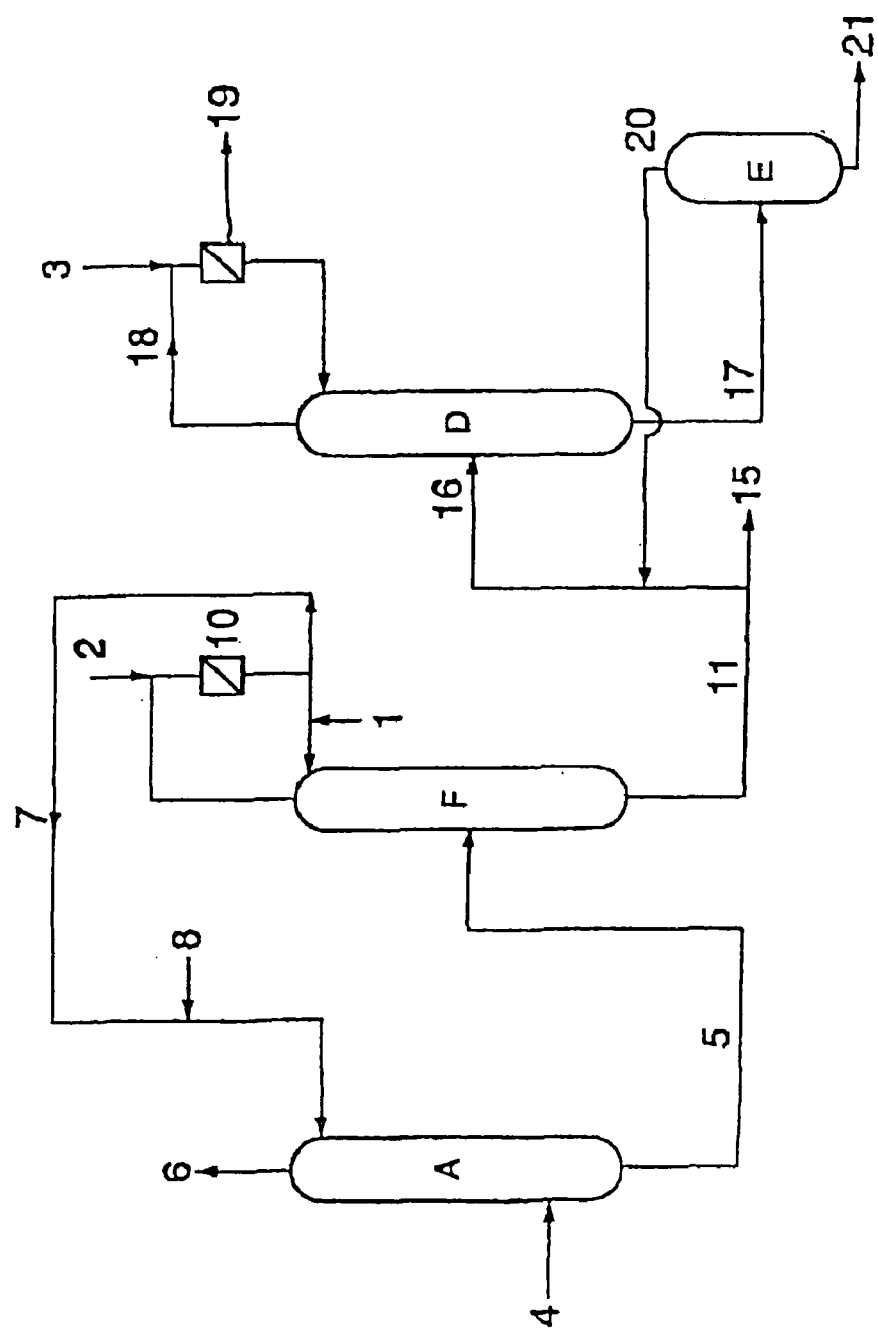
FIG. 2 is another example of a process flow chart for producing acrylic acid by using propylene as the starting material.

FIG. 2 is another example of a process flow chart for producing acrylic acid.

This is a process having the dehydration column B and the low boiling separation column (acetic acid separation column) C in FIG. 1 joined into one column i.e. a distillation column F, whereby the flow of the substances is basically the same as in FIG. 1.

Figure 3:
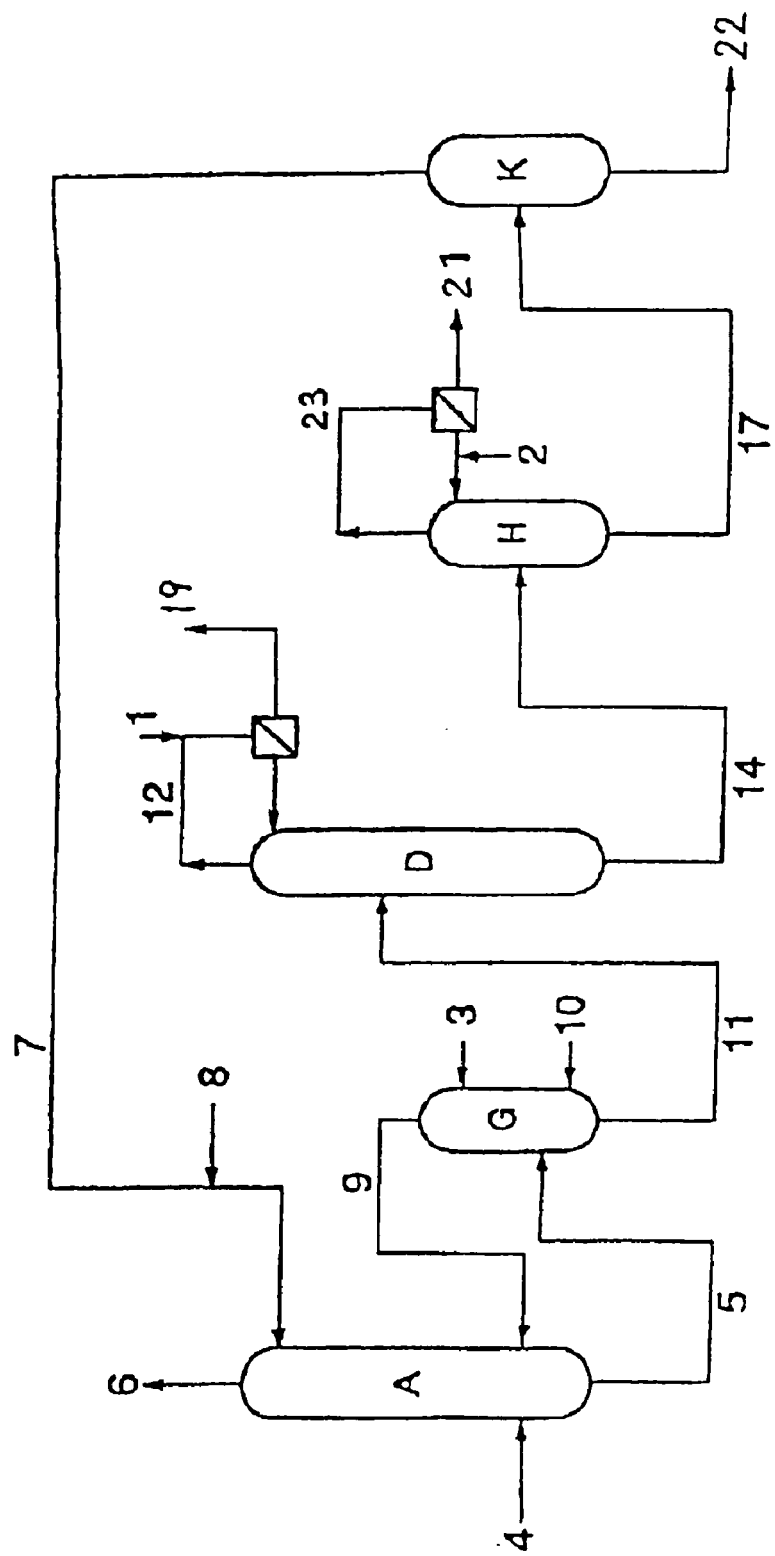
FIG. 3 is another example of a process flow chart for producing acrylic acid by using propylene as the starting material.

FIG. 3 is another example of a process flow chart for producing acrylic acid.

A: Acrylic acid collection column
G: Desorption column
D: High boiling separation column (acrylic acid purification column)
H: High boiling removal column
K: Solvent recovery column
1 to 3: Washing solution or polymerization inhibitor-supply line
4: Oxidation reaction gas containing acrylic acid
5: Acrylic acid-containing solution
11: Crude acrylic acid
19: High purity acrylic acid-discharge line The acrylic acid-containing gas obtained by vapor phase catalytic oxidation of propylene and/or acrolein by means of a molecular oxygen-containing gas, is introduced via a line 4 into the acrylic acid collection column A and contacted with a solvent to obtain an acrylic acid-containing solution.

Then, the acrylic acid-containing solution is supplied to the desorption column G. In the desorption column G, a gas (a gas of a line 6 discharged from the top of the acrylic acid collection column A, or a gas after oxidizing and removing organic substances in the gas in the line 6) is supplied from a line 10, water and acetic acid are distilled from the column top, and acrylic acid containing the solvent is obtained from the column bottom. Water and acetic acid distilled from the top of the desorption column G are introduced into the acrylic acid collection column A, and water and acetic acid are finally discharged from the top of the acrylic acid collection column A. In order to obtain high purity acrylic acid, acrylic acid from the bottom of the desorption column G is introduced via a line 11 into a high boiling separation column (acrylic acid purification column) D, whereby high boiling substances are separated and removed from a line 14, and high purity acrylic acid can be obtained via a line 19. The high boiling substances in the line 14 are specifically maleic anhydride, benzaldehyde, etc., and they are led to a high boiling removal column H, whereupon these high boiling point substances are discharged from a line 21. The solvent from the column bottom is led via a line 17 to a solvent recovery column K. From the column top, the recovered solvent is returned via a line 7 to the acrylic acid collection column A. From the column bottom, via a line 22, higher boiling substances are separated and removed.

Figure 4:
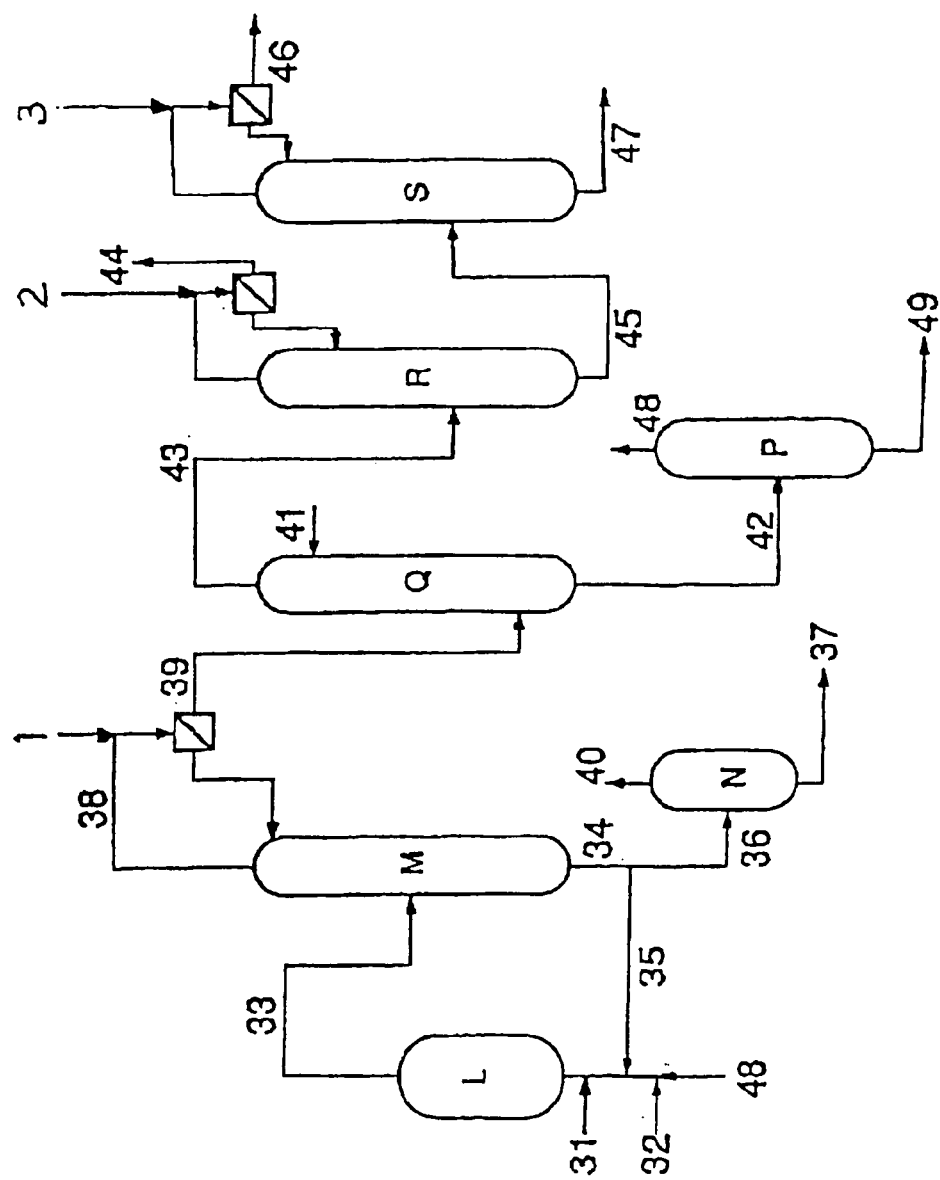
FIG. 4 is an example of a process flow chart for producing an acrylic acid ester.

FIG. 4 is an example of a process flow chart for producing an acrylic acid ester. The symbols and numbers in the Fig. are as follows.

L: Esterification reactor
M: Acrylic acid separation column
N: High boiling decomposition reactor
Q: Alcohol extraction column
P: Alcohol recovery column
R: Low boiling separation column
S: Ester purification column
31: Acrylic acid-supply line
32: Alcohol-supply line
33: Esterification reaction mixture
35: Recycled acrylic acid
37: High boiling impurity-discharge line
39: Crude acrylic acid ester-discharge line
41: Water supply line
42: Recovered alcohol/water line
46: Acrylic acid ester product-discharge line Acrylic acid from the line 31, the alcohol from the line 32, the recycled acrylic acid from the line 35 and the recycled alcohol from the line 48 are, respectively, supplied to the esterification reactor L. In the esterification reactor L, a catalyst such as a strongly acidic ion exchange resin is packed. Via the line 33, the esterification reaction mixture comprising the formed ester, unreacted acrylic acid, an unreacted alcohol and formed water, is withdrawn and supplied to the acrylic acid separation column M. From the acrylic acid separation column M, the bottom liquid containing substantially the entire amount of unreacted acrylic acid, is withdrawn via a line 34 and supplied as a recycled liquid via the line 35 to the esterification reactor L.

A part of the bottom liquid is supplied via a line 36 to the high boiling decomposition reactor N, and a valuable substance obtained by the decomposition is recycled via a line 40 to the process. The place within the process where it is recycled, varies depending upon the process conditions. High boiling impurities such as oligomers, will be removed out of the system via the line 37. Further, from the top of the acrylic acid separation column M, the formed ester, an unreacted alcohol and formed water are distilled via a line 38. A part of the distillate will be recycled as a reflux liquid to the acrylic acid separation column M, and the rest will be supplied via the line 39 to the extraction column Q.

From the line 41, water for extraction of the alcohol is supplied, and the water containing the recovered alcohol will be supplied via the line 42 to the alcohol recovery column P. The recovered alcohol is recycled via a line 48 to the esterification reactor.

From a line 43, the crude acrylic acid ester is supplied to the low boiling separation column R. Low boiling substances containing the acrylic acid ester are withdrawn from a line 44 and will be recycled to the process. The place within the process where it is recycled, varies depending upon the process conditions. The crude acrylic acid ester having the low boiling substances removed, will be supplied via a line 45 to the acrylic acid ester product purification column S. From the column top, high purity acrylic acid ester is obtained via the line 46. From the column bottom, a liquid containing some high boiling substances will be discharged via a line 47 and recycled to the process. The place within the process where it is recycled, varies depending upon the process conditions.

Figure 5:
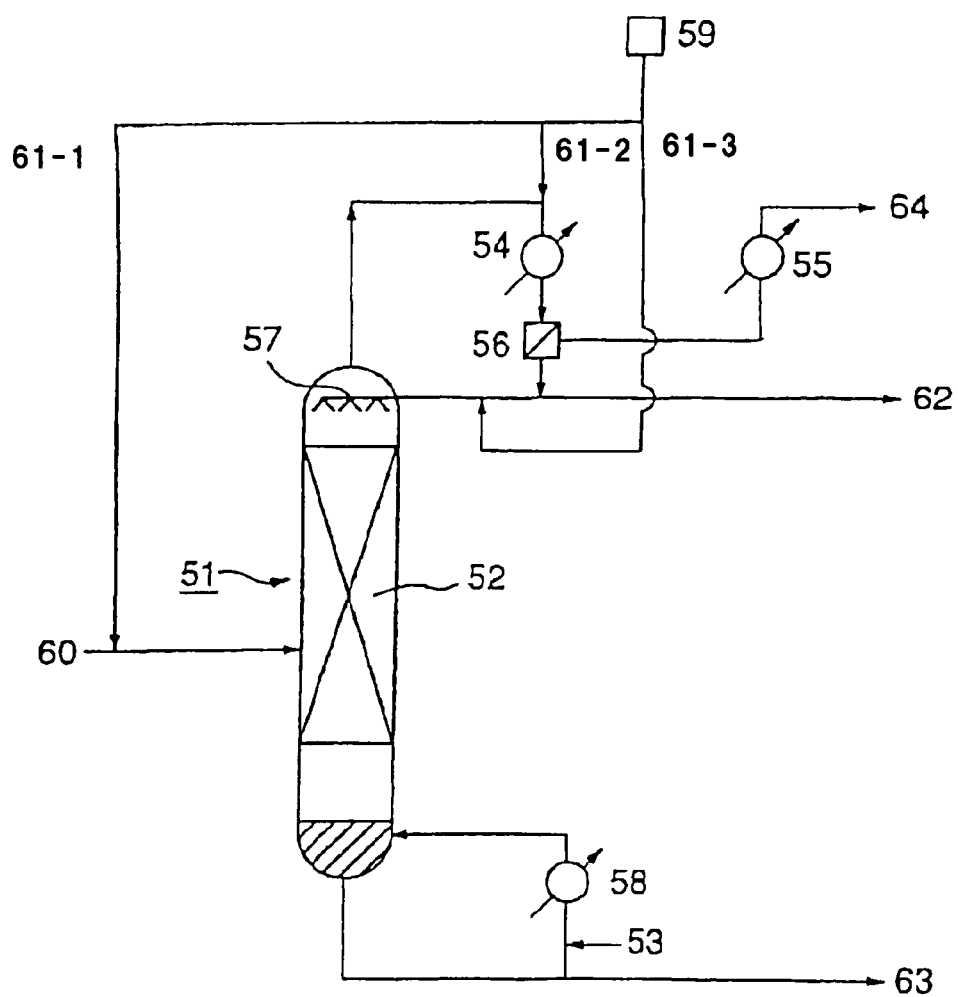
FIG. 5 is an example of a distillation column for a crude (meth)acrylic acid compound and its incidental facilities.

FIG. 5 is an example of a distillation column for crude acrylic monomer and its incidental facilities. The numbers in the Fig. are as follows.

51: Distillation column
52: Packing material layer or distillation column trays, or combination of packing material and distillation column trays
53: Inhibitor air-supply line
54: Heat exchanger for cooling the column top gas
55: Heat exchanger for cooling the vent gas
56: Reflux drum
57: Distributor
58: Reboiler (heat exchanger for heating)
59: Washing solution or polymerization inhibitor-containing liquid tank
60: Acryl monomer (raw material)-supply line
61: Washing solution or polymerization inhibitor-supply line
62: Column top liquid-discharge line
63: Column bottom liquid-discharge line
64: Vent gas-discharge line The line 53 and the lines 61 may be installed at one or more locations at various portions of distillation depending upon the conditions of the distillation column.

The distillation column to which the present invention can be applied, is all types of distillation apparatus wherein (meth)acrylic acid compounds are involved in vapor-liquid equilibrium and is meant for any apparatus to carry out an operation such as separation, concentration, recovery, purification, etc. For example, the dehydration column B, the low boiling separation column (acetic acid separation column) C and the high boiling separation column (acrylic acid purification column) D, shown in FIG. 1, correspond thereto. Likewise, the desorption column G, the high boiling separation column (acrylic acid purification column) D, the high boiling removal column H and the solvent recovery column K, shown in FIG. 3, and the acrylic acid separation column M, the alcohol recovery column P, the low boiling separation column R and the ester purification column S, shown in FIG. 4, and the distillation column 51 shown in FIG. 5, correspond thereto.

The distillation column may, for example, be a perforated plate column, a bubble column, a packed column or a combination thereof (such as a combination of a perforated plate column and a packed column, see FIG. 5), and any of them may be used in the present invention irrespective of the presence or absence of an overflow gate or a downcomer. Specific trays may, for example, be bubble cap trays, perforated plate trays, bubble trays, super flash trays, max flux trays, or dual trays.

As the packing material, in addition to conventional ones of e.g. columnar, cylindrical, saddle-type, spherical, cubic or pyramid-shaped, a packing material having a special shape and having a regular or irregular shape, is commercially available as a high performance packing material in recent years. Such a material can preferably be used in the present invention. Such commercial products may, for example, be, as a regular packing material, a gauze type regular packing material such as Sulzer Packing (manufactured by Sulzer Brothers Company), Sumitomo Sulzer Packing (manufactured by Sumitomo Heavy Industries, Ltd.) or Tecknopack (manufactured by Mitsui & Co., Ltd.), or MC Pack (manufactured by Mitsubishi Chemical Engineering Corporation), a sheet type regular packing material such as Mellapack (manufactured by Sumitomo Heavy Industries, Ltd.), Tecknopack (manufactured by Mitsui & Co., Ltd.), or MC Pack (manufactured by Mitsubishi Chemical Engineering Corporation), or a grid type regular packing material such as Flexigrid (manufactured by Koch Company). As other packing materials, GEMPAK (manufactured by Glitsch Company), Montz Pack (manufactured by Montz Company), Goodroll Packing (manufactured by Tokyo Tokushu Kanaami K.K.), Honeycomb Pack (Manufactured by NGK Insulators, Ltd.) or Impulse Packing (Manufactured by Nagaoka Corporation) may, for example, be mentioned.

Further, as an irregular packing material, Raschig ring, Pall ring (manufactured by BASF), Cascade Miniring (manufactured by Mass Transfer Company), IMTP (manufactured by Norton Company), Intalox Saddle (manufactured by Norton Company), Tellerette (manufactured by Nittetsu Chemical Engineering Ltd.) or Flexiring (manufactured by JGC Corporation) may, for example, be mentioned.

A feature in the present invention resides in that at the time of washing a polymer deposited and accumulated in the distillation column after operating the distillation column for a (meth)acrylic acid compound for a predetermined period of time, (1) after washing with water, (2) inside flow-down washing with an organic solvent and/or (3) azeotropic distillation in the presence of an organic solvent, is carried out. Prior to (2) and/or (3), (4) washing with alkaline water may be carried out, and such washing with alkaline water is effective for dissolving the polymer. When washing with alkaline water is carried out, it is important to additionally provide (5) a step of washing with water thereafter. Now, the process will be sequentially described.

(1) Washing with Water

It is the main purpose of water to wash out the (meth) acrylic acid compound remaining in the column. Water is supplied to the reflux drum of the distillation column and supplied to the top of the distillation column from the reflux line, or it may be supplied from the reflux line directly to the distillation column. The water flows down to the bottom while washing the interior of the column. In order to let water sufficiently contact the polymer in the column, the wall of the column, the packing material in the column, etc. water supplied from the column top and flows down to the column bottom may be repeatedly supplied from the column top. In the case of repeated supply, it is preferred to use the water after separating and removing the solid content in the flowed down water by e.g. a strainer of a pump. Together with the supply from the column top, additional supply can be made from the material supply-stage.

In a case where a distributor (a liquid distributor or a liquid distributing nozzle) is installed at an upper portion of the packed column, it is preferred to adopt a method of supplying water via such a distributor.

Washing with water may be carried out usually at a temperature of from 10 to 100° C. for from 30 to 360 minutes. The amount of water to be supplied may depend also on the degree of clogging or stain in the column, but is usually from about 0.5 to 5 m$^3$/hr per 1 m$^2$ of the cross-sectional area of the distillation column (when the water is repeatedly used, the integrated value thereof).

In the washing solution thus recovered at the column bottom, a valuable substance (such as acrylic acid or an acrylic acid ester) which was remaining in the distillation column immediately after suspension of the operation, is contained. Accordingly, the washing solution is once transferred to and stored in a tank, and after resumption of the operation of the distillation column, it will be recycled to a proper position within the process (such as the dehydration column B in FIG. 1) taking into consideration the composition of the washing solution.

(2) Inside Flow-Down Washing with Organic Solvent

The inside washing with an organic solvent is intended for substitution of water remaining in the column. The organic solvent to be used for the inside washing, may, for example, be a (meth)acrylic acid compound, methanol, ethanol, butanol, benzene, toluene, methyl ethyl ketone, methyl isobutyl ketone, methyl n-butyl ketone, isopropyl acetate, diphenyl ether, biphenyl, or a mixture thereof.

As the organic solvent of the present invention, not only a high purity solvent as mentioned above, but also an organic solvent type substance containing various azeotropic agents obtainable from a process before or after the distillation column, may also be efficiently used. For example, it is possible to use the azeotropic agent used for concentration of the aqueous solution containing (meth)acrylic acid, the crude (meth)acrylic acid obtained by such concentration, the purified (meth)acrylic acid compound (product) obtained prior to the suspension of operation of the distillation column, or an off-specification product recovered at the time of suspension of the plant.

The water content in the organic solvent to be used is preferably at most 2 wt %, more preferably at most 1 wt %. For example, the product of the (meth)acrylic acid compound usually has a water content of at most 0.2 wt %, and accordingly, such a product can be used as it is. Specifically, in the above-mentioned process charts, it is preferably used for C and D in FIG. 1, D in FIG. 2 and S in FIG. 3.

The method for substitution of water by the inside washing is not particularly limited. For example, it is preferred that the organic solvent is supplied to a reflux drum of a distillation column and supplied from a reflux line to the top portion of the distillation column. The organic solvent which flowed down to the bottom while contacted with the column wall, the packing material, the trays, etc. to include water, may be withdrawn to a recovery system, but in order to carry out sufficient removal of water, it is preferred to recycle it to the column top or to the material-supply stage. If the water content in the organic solvent to be recycled exceeds 2 wt %, the dehydration effect will be substantially lowered, and such an organic solvent is withdrawn out of the system. The inside washing with an organic solvent is usually carried out at a temperature of at most 50° C., preferably within a range of from 0 to 40° C.

The amount of the organic solvent to be used may usually be from 0.5 to 5 m$^3$/hr per 1 m$^2$ of the cross-sectional area of the distillation column. In a case where removal of the residual water is difficult from the structure of the interior of the distillation column, the flow rate may optionally be increased.

(3) Azeotropic Distillation Cleaning in the Presence of Organic Solvent

In the present invention, in order to remove water present in the column after washing with water, azeotropic distillation cleaning is carried out in the presence of an organic solvent which can be azeotropically distilled with water. This step is intended to remove water, but in a case where a small amount of a polymer is remaining in the column, its dissolution and removal may be simultaneously carried out. The water is distilled off from the top, and the dissolved polymer, etc. will be withdrawn from the bottom.

Useful organic solvents include alcohols such as methanol, ethanol and butyl alcohol, ketones such as methyl ethyl ketone, methyl-n-butyl ketone and methyl isobutyl ketone, aromatic hydrocarbons such as benzene, toluene and xylene, and the above-mentioned (meth)acrylic acid compounds. These organic solvents may be used in combination as a mixture.

Such an organic solvent is supplied to the stage for supplying the distillation stock solution or to the bottom of the column and will be treated under distillation conditions by a heat source from a reboiler. As such conditions, the column top temperature is preferably from 20 to 80° C., and the column top pressure is preferably from 0.5 to 120 kPa. The water content of the organic solvent is preferably maintained to be at most 2 wt %, more preferably at most 1 wt %, whereby the dehydration efficiency will be excellent.

(4) Washing with Alkaline Water

In the present invention, washing with alkaline water is not an essential step. However, it is thereby possible to dissolve an acidic polymer and to increase the washing effects. Accordingly, it may optionally be incorporated as a preliminary step and/or a subsequent step, of washing with water. In a case where washing with alkaline water is incorporated, the distillation operation will be resumed after a step of washing with water and a dehydration step subsequent thereto.

As the alkaline water, an aqueous solution of e.g. potassium hydroxide, sodium hydroxide or sodium carbonate, may be used. With respect to the concentration, it is used usually within a range of from 1 to 25 wt %. Further, aqueous ammonia may be used, and with respect to the concentration, it is used usually within a range of from 1 to 25 wt %, preferably within a range of from 1 to 10 wt %. If the concentration is lower than the above range, the washing efficiency tends to be poor, and if it exceeds the above range, the heat of reaction with the acid component remaining in the column tends to increase, whereby formation of a new polymer is likely to result.

The alkaline water may be supplied to a reflux drum of a distillation column and supplied by a reflux line to the top of the distillation column, or may be supplied directly to the distillation column from a reflux line. The alkaline water flows down to the bottom while swelling and dissolving the inside polymer. In order to let it sufficiently contact with the inside polymer, the wall of the column, the packing material in the column, etc., the alkaline water supplied from the top and flows down to the bottom, may repeatedly be supplied from the column top. In the case of repeated supply, it is preferred to use it after separating and removing solid substances contained in the flowed down alkaline water by e.g. a strainer of a pump. Together with the supply from the column top, additional supply may be made from the raw material supply stage.

In a case where a distributor (a liquid distributor or a liquid distributing nozzle) is installed at an upper portion of the packed column, it is preferred to adopt a method of supplying alkaline water via such a distributor.

Washing with alkaline water may be carried out usually at a temperature of from 10 to 100° C. for from 30 to 360 minutes. The amount of alkaline water to be supplied may depend also on the degree of clogging or stain in the column, but is usually preferably from about 0.5 to 5 m$^3$/hr per 1 m$^2$ of the cross-sectional area of the distillation column (in the case where alkaline water is used repeatedly, the integral value thereof).

(5) Washing with Water

In a case where the above-mentioned washing with alkaline water is carried out, it is important to additionally carry out washing with water in order to remove the remaining alkali. The method for washing with water in this case is the same as (1) washing with water described in the paragraph [0024].

The water remaining in the column by the inside flow down washing with an organic solvent or by the azeotropic distillation cleaning in the presence of an organic solvent, is usually at most 1 wt %, preferably at most 0.5 wt %, more preferably substantially 0. Thus, after resumption of the distillation operation, on-specification distillation will be quickly possible. If water is remaining, it will be often a case it takes a long time at a level of 30 hours until an on-specification state will be reached.

At the time of the above-mentioned azeotropic distillation cleaning, a small amount of a polymerization inhibitor may be supplied. Such a polymerization inhibitor (which may also be called as a polymerization-suppressing agent, a polymerization-inhibiting agent, a polymerization-stopping agent or a polymerization rate-reducing agent) may, for example, be a phenol compound such as a hydroquinone, methoquinone (methoxyhydroquinone), pyrogallol, catechol or resorcinol; an N-oxyl compound such as tertiary butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidinooxyl, 4-hydroxy-2,2,6,6-tetramethylpiperidinooxyl, or 4,4',4"-tris-(2,2,6,6-tetramethylpiperidinooxyl)phosphite; a phenothiazine compound such as phenothiazine, bis-α-methylbenzyl)phenothiazine, 3,7-dioctylphenothiazine or bis-(α,α'-dimethylbenzyl)phenothiazine; a copper compound such as cupric chloride, copper acetate, copper carbonate, copper acrylate, copper dimethyldithiocarbamate, copper diethyldithiocarbamate, copper dibutyldithiocarbamate or copper salicylate; a manganese salt compound such as manganese acetate; a phenylene diamine such as p-phenylene diamine; a nitroso compound such as N-nitrosodiphenylamine; an urea such as urea; or a thiourea such as thiourea. These compounds may be used alone or in combination as a mixture of two or more of them.

After completion of the washing operation, a prescribed distillation stock solution containing a crude (meth)acrylic acid compound is supplied to resume the distillation operation. This distillation may be carried out by continuous distillation or batch distillation. The operation conditions for the distillation are optionally determined taking into consideration the types or contents of the impurities contained in the crude (meth)acrylic acid compound, etc., and they are not particularly limited. Usually, the distillation is carried out at a column top temperature of from 20 to 80° C., at a column bottom temperature of from 60 to 120° C. and under a column top pressure of from about 0.5 to 120 kPa.

Now, the present invention will be described in further detail with reference to Examples. However, it should be understood that the present invention is not limited to such Examples unless it exceeds beyond its gist.

EXAMPLE 1

After an inside inspection of a high boiling separation column (acrylic acid purification column) D in FIG. 1, of which the operation was suspended for a periodic inspection, an operation for resumption of the operation was carried out. After the inside inspection of the high boiling separation column D, the inside was washed with water to remove the stain formed during the operation.

The high boiling separation column was a distillation column made of stainless steel (SUS316) having an internal diameter of 1100 mm and a height of 20000 mm and having 21 perforated plates, and using such a column, distillation of crude acrylic acid was carried out. Prior to the distillation, 1000 kg of an acrylic acid product containing 0.03 wt % of water, supplied to a reflux drum 56, was supplied to the high boiling separation column from the top. The supplied liquid flowed down to the bottom, and the liquid collected at the bottom was discharged from the bottom portion of the column. The water content of the discharged acrylic acid was 3 wt %.

Therefore, 1000 kg of the same acrylic acid product was again supplied to the reflux drum 56, and a similar washing and substitution operation was carried out. The water content in the acrylic acid discharged from the bottom was 0.2 wt %. From the starting material supply line 60, a mixture comprising 98.5 wt % of acrylic acid as a crude acryl monomer, 0.3 wt % of maleic acid, 0.2 wt % of an acrylic acid dimer, 0.02 wt % of water and other high boiling substances, was supplied at a rate of 1300 kg/hr. Further, from the tank 59 for a polymerization inhibitor-containing liquid, liquids having 8 wt % of methoquinone and 1 wt % of phenothiazine dissolved in acrylic acid, were supplied at rates of 34 kg/hr and 31 kg/hr, respectively. The heat source was supplied, and the inside pressure, etc. were adjusted, and after about 5 hours, the operation became stable at a column top pressure of 2.8 kPa at a bottom pressure of 8.4 kPa at a column top temperature of 53° C. and a bottom temperature of 78° C. from the column top, high purity acrylic acid having a water content of 0.02 wt % and a purity of at least 99.8 wt %, was obtained. With respect to the operation, a continuous operation for 1 year was possible.

COMPARATIVE EXAMPLE 1

Distillation was resumed in the same manner as in Example 1 except that in Example 1, inside substitution with acrylic acid was omitted. In the acrylic acid obtained from the top of the column by the resumption of the operation, 0.7 wt % of water was contained. The water content gradually decreased, and about 36 hours were required until the water content became 0.02 wt %. As the distillation was continued under the water excessive state, the bottom pressure of the distillation column gradually increased, and after one month, the bottom pressure became 18 kPa, whereby the operation was terminated. As a result of the internal inspection, a large amount of a polymer was detected.

EXAMPLE 2

After an inside inspection of a low boiling separation column R in FIG. 4, of which the operation was suspended for a periodic inspection, an operation for resumption of the operation was carried out. After the inside inspection of the low boiling separation column R, the inside was washed with water to remove the stain during the operation.

The low boiling separation column R was a distillation column as shown in FIG. 5, made of stainless steel (SUS304) and having an internal diameter of 1100 mm and a height of 26000 mm and having 36 perforated plates (dual trays) installed inside, and using such a column, a distillation of crude ethyl acrylate was carried out.

Prior to the distillation, 800 kg of an ethyl acrylate product having a water content of 0.002 wt %, supplied to a reflux drum 56, was supplied to the low boiling separation column from the top. The supplied liquid flowed down to the bottom, and the liquid collected at the bottom portion was discharged therefrom. The water content of the discharged ethyl acrylate was 3.6 wt %.

Therefore, 1000 kg of the same ethyl acrylate product was supplied again to the reflux drum 56, and a similar washing and substitution operation was carried out. The water content in the ethyl acrylate discharged from the bottom was 0.11 wt %. A similar operation was conducted again, and as a result, the water content in the ethyl acrylate discharged from the bottom was 0.004 wt %. A mixture comprising 97.4 wt % of ethyl acrylate as the crude acryl monomer, 1.8 wt % of water, 0.4 wt % of acrylic acid, 0.4 wt % of ethanol and 0.1 wt % of ethyl acetate, was supplied at a rate of 6000 kg/hr. Further, from a tank 59 for a polymerization inhibitor-containing liquid, a liquid having 5 wt % of hydroquinone dissolved in ethanol, was supplied at a rate of 60 kg/hr. A heat source was supplied, and the inside pressure, etc. were adjusted, and after about 7 hours, the operation became stable at a column top pressure of 62.7 kPa at a bottom pressure of 72.7 kPa at a column temperature of 76° C. and a bottom temperature of 89° C. Ethyl acrylate having a water content of 0.001 wt % and a purity of at least 99.1 wt %, was obtained from the bottom. During the operation, the difference in pressure between the column top and the column bottom (hereinafter referred to as the pressure difference) was stable during the operation, and a continuous operation for one year was possible.

COMPARATIVE EXAMPLE 2

The distillation was resumed in the same manner as in Example 2 except that in Example 2, the inside substitution with ethyl acrylate was omitted. Initially, ethyl acrylate obtained from the bottom contained 3.1 wt % of water. The water content gradually decreased, and about 53 hours were required until the water content became 0.001 wt %. The distillation was continued under a water excessive state, whereby from the resumption of the operation, the bottom pressure of the distillation column gradually increased, and after one month, the bottom pressure became 82 kPa, whereby the operation was terminated. As a result of the inside inspection, a large amount of a polymer was detected.

EXAMPLE 3

After an inside inspection of a dehydration column B in FIG. 1, of which the operation was suspended for a periodic inspection, an operation for resumption of the operation was carried out. After the inside inspection of the dehydration column B, the inside was washed with water in order to remove the stain during the operation.

The dehydration column B was a distillation column made of stainless steel (SUS316L), having an internal diameter of 4000 mm and a height of 25000 mm and having 30 perforated plates, and using such a column, distillation of crude acrylic acid was carried out.

Prior to the distillation, toluene was supplied to the reflux drum at a rate of 5000 kg/hr and supplied to the high boiling separation column from the top. The supplied liquid flowed down to the column bottom, and after confirming the liquid surface at the bottom, a heat source was supplied. From the column top, distilled toluene and water were discharged. After about 5 hours, there was no more distillation of water. During this period, there was no discharge from the bottom.

From the starting material supply line, a mixture comprising 60 wt % of acrylic acid as a crude acryl monomer, 0.4 wt % of maleic acid, 4 wt % of acetic acid, 35 wt % of water and other high boiling substances, was supplied at a rate of 7500 kg/hr. Further, from the drum for a polymerization inhibitor-containing liquid, a liquid having 0.6 wt % of copper acetate and 4 wt % of hydroquinone dissolved in acrylic acid was supplied at a rate of 6 kg/hr, and a liquid having 2 wt % of phenothiazine dissolved in toluene, was supplied at a rate of 500 kg/hr. At the same time, supply of toluene from the reflux drum was stopped, and toluene distilled from the column top was refluxed and balanced to maintain the liquid level of the reflux drum, while a part was withdrawn out of the system.

A heat source was supplied, and the inside pressure, etc. were adjusted, and after about 6 hours, the operation became stable at a column top pressure of 15.9 kPa at a bottom pressure of 22.7 kPa at a column top temperature of 46° C. and a bottom temperature of 82° C. From the bottom, acrylic acid having a water content of 0.01 wt % and a purity of at least 74 wt %, was obtained. With respect to the operation, a continuous operation for one year was possible.

COMPARATIVE EXAMPLE 3

The distillation was resumed in the same manner as in Example 3 except that in Example 3, the initial distillation by toluene was omitted. At the resumption of the operation, acrylic acid obtained from the bottom contained 2 wt % of water. The water content gradually decreased, and about 62 hours were required until the water content became 0.01 wt %.

INDUSTRIAL APPLICABILITY

By employing the process of the present invention, washing of a distillation column for separating or purifying a (meth)acrylic acid compound can be carried out easily. Particularly, in a process for producing a (meth)acrylic acid compound, it is possible to recover a valuable substance and to effectively wash the distillation column by utilizing a substance used in a process before or after the distillation column. Further, at the resumption of the distillation operation after the washing, on-specification stabilized operation will quickly become possible.

The entire disclosure in the specification of Japanese Patent Application No. 2002-257275 from which the priority is claimed in this application, is incorporated herein by reference in its entirety.

What is claimed is:

1. A process for producing a (meth)acrylic acid compound, comprising:
    distilling (meth)acrylic acid or an ester thereof in a distillation column to obtain a purified (meth)acrylic acid compound,
    wherein in the course of operation of the distillation column including suspension and resumption of the operation, the distillation column is washed with water and, thereafter, inside washing with an organic solvent and/or azeotropic distillation in the presence of the organic solvent is conducted.

2. A process for producing (meth)acrylic acid, comprising:
subjecting propylene, propane or isobutylene to vapor phase catalytic oxidation to obtain an oxidized reaction mixture,
absorbing the oxidized reaction product in water to obtain an aqueous solution containing (meth)acrylic acid,
concentrating the aqueous solution in the presence of an azeotropic agent, and
distilling the obtained (meth)acrylic acid in a distillation column to obtain purified (meth)acrylic acid,
wherein in the course of operation of the distillation column including suspension and resumption of the operation, the distillation column is washed with water and, thereafter, azeotropic distillation is conducted in the presence of the azeotropic agent.

3. A process for producing (meth)acrylic acid, comprising:
subjecting propylene, propane or isobutylene to vapor phase catalytic oxidation to obtain an oxidized reaction mixture,
absorbing the oxidized reaction product in water to obtain an aqueous solution containing (meth)acrylic acid,
concentrating the aqueous solution in the presence of an azeotropic agent, and
distilling the obtained (meth)acrylic acid in a distillation column to obtain purified (meth)acrylic acid,
wherein in the course of operation of the distillation column including suspension and resumption of the operation, the distillation column is preliminarily washed with water, then, with alkaline water and with water and, thereafter, azeotropic distillation is conducted in the presence of the azeotropic agent.

4. The process according to claim 1, wherein the organic solvent has a water content of at most 2 wt %.

5. The process according to claim 1, wherein the organic solvent is a (meth)acrylic acid compound, methanol, ethanol, butanol, benzene, toluene, methyl ethyl ketone, methyl isobutyl ketone, methyl n-butyl ketone, isopropyl acetate, diphenyl ether, biphenyl or a mixture thereof.

6. The process according to claim 1, wherein the azeotropic distillation is conducted at a column top temperature of from 20 to 80° C. under a column top pressure of from 0.5 to 120 kPa.

7. The process according to claim 1, wherein the azeotropic distillation is conducted in the presence of a polymerization inhibitor.

8. A process for producing a (meth)acrylic acid ester, comprising:
subjecting propylene, propane or isobutylene to vapor phase catalytic oxidation to obtain an oxidized reaction mixture,
absorbing the oxidized reaction product in water to obtain an aqueous solution containing (meth)acrylic acid,
concentrating the aqueous solution in the presence of an azeotropic agent, and
purifying the obtained (meth)acrylic acid in a distillation column and then reacting it with an alcohol to obtain an ester, and purifying the ester in a distillation column to obtain a purified (meth)acrylic acid ester,
wherein in the course of operation of the distillation column including suspension and resumption of the operation, the distillation column is washed with water and, thereafter, inside washing with an organic solvent and/or azeotropic distillation in the presence of the organic solvent is conducted.

9. A process for producing a (meth)acrylic acid ester, comprising:
subjecting propylene, propane or isobutylene to vapor phase catalytic oxidation to obtain an oxidized reaction mixture,
absorbing the oxidized reaction product in water to obtain an aqueous solution containing (meth)acrylic acid,
concentrating the aqueous solution in the presence of an azeotropic agent, and
purifying the obtained (meth)acrylic acid in a distillation column and then reacting it with an alcohol to obtain an ester, and purifying the ester in a distillation column to obtain a purified (meth)acrylic acid ester,
wherein in the course of operation of the distillation column including suspension and resumption of the operation, the distillation column is preliminarily washed with water, then, with alkaline water and with water and, thereafter, azeotropic distillation is conducted in the presence of an organic solvent.

10. The process according to claim 2, wherein the azeotropic distillation is conducted at a column top temperature of from 20 to 80° C. under a column top pressure of from 0.5 to 120 kPa.

11. The process according to claim 2, wherein the azeotropic distillation is conducted in the presence of a polymerization inhibitor.

12. The process according to claim 3, wherein the azeotropic distillation is conducted at a column top temperature of from 20 to 80° C. under a column top pressure of from 0.5 to 120 kPa.

13. The process according to claim 3, wherein the azeotropic distillation is conducted in the presence of a polymerization inhibitor.

* * * * *